(12) United States Patent
Fisher et al.

(10) Patent No.: US 8,211,154 B2
(45) Date of Patent: Jul. 3, 2012

(54) BONE PLATE ASSEMBLIES WITH BACKOUT PROTECTION AND VISUAL INDICATOR

(75) Inventors: James Fisher, Broomfield, CO (US);
Alan Burkholder, Denver, CO (US);
Michael Fulton, Centennial, CO (US)

(73) Assignee: Lanx, Inc., Broomfield, CO (US)

( * ) Notice: Subject to any disclaimer, the term of this patent is extended or adjusted under 35 U.S.C. 154(b) by 402 days.

(21) Appl. No.: 12/419,012

(22) Filed: Apr. 6, 2009

(65) Prior Publication Data

US 2010/0256686 A1  Oct. 7, 2010

(51) Int. Cl.
*A61B 17/80* (2006.01)

(52) U.S. Cl. ......... 606/293; 606/289; 606/290; 606/294

(58) Field of Classification Search .................. 606/280, 606/70, 712, 89, 290, 293–296, 305, 308; 411/85, 95, 96, 97, 342, 349, 552, 553, 352, 411/353, 371.1, 371.2

See application file for complete search history.

(56) References Cited

U.S. PATENT DOCUMENTS

| | | |
|---|---|---|
| 2,409,638 A | 10/1946 | Lyon |
| 3,486,505 A | 12/1969 | Morrison |
| 3,711,347 A | 1/1973 | Wagner et al. |
| 3,750,652 A | 8/1973 | Sherwin |
| 3,834,021 A | 9/1974 | White et al. |
| 4,794,918 A | 1/1989 | Wolter |
| 5,085,660 A | 2/1992 | Lin |
| 5,364,399 A | 11/1994 | Lowery et al. |
| 5,407,312 A | 4/1995 | Terrizzi |
| 5,558,674 A | 9/1996 | Heggeness et al. |
| 5,578,034 A | 11/1996 | Estes |
| 5,676,666 A | 10/1997 | Oxland et al. |
| 5,741,258 A | 4/1998 | Klaue et al. |
| 5,782,830 A | 7/1998 | Farris |
| 5,885,299 A | 3/1999 | Winslow et al. |
| 5,904,683 A | 5/1999 | Pohndorf et al. |
| 5,951,558 A | 9/1999 | Fiz |
| 5,954,722 A | 9/1999 | Bono |
| 5,957,927 A | 9/1999 | Magee et al. |
| 6,129,730 A | 10/2000 | Bono et al. |
| 6,139,550 A | 10/2000 | Michelson |
| 6,152,927 A | 11/2000 | Farris et al. |
| 6,159,213 A | 12/2000 | Rogozinski |
| 6,193,721 B1 | 2/2001 | Michelson |
| 6,224,599 B1 | 5/2001 | Baynham et al. |
| 6,224,602 B1 | 5/2001 | Hayes |
| 6,235,033 B1 | 5/2001 | Brace et al. |

(Continued)

FOREIGN PATENT DOCUMENTS

WO  WO 99/56653  11/1999

*Primary Examiner* — Andrew Yang

(74) *Attorney, Agent, or Firm* — Holland & Hart LLP

(57) ABSTRACT

A bone plate assembly includes a plate, at least one bushing, and at least one bone screw. The bushing is positioned within a through hole of the plate. The bushing and screw are configured to engage each other to inhibit the screw from backing out. The screw includes a visual indicator surface that is visible to the operator during insertion of the screw through the bushing and plate. The bushing is configured to cover at least a portion of the visual indicator surface to show when the bushing and screw are properly engaged to inhibit backout of the screw.

19 Claims, 10 Drawing Sheets

U.S. PATENT DOCUMENTS

| | | |
|---|---|---|
| 6,235,034 B1 | 5/2001 | Bray |
| 6,258,089 B1 | 7/2001 | Campbell et al. |
| 6,261,291 B1 | 7/2001 | Talaber et al. |
| 6,261,296 B1 | 7/2001 | Aebi et al. |
| 6,306,139 B1 | 10/2001 | Fuentes |
| 6,413,259 B1 | 7/2002 | Lyons et al. |
| 6,436,101 B1 | 8/2002 | Hamada |
| 6,503,250 B2 | 1/2003 | Paul |
| 6,533,786 B1 | 3/2003 | Needham et al. |
| 6,565,303 B1 | 5/2003 | Riccitellie et al. |
| 6,602,255 B1 * | 8/2003 | Campbell et al. ............ 606/290 |
| 6,626,907 B2 | 9/2003 | Campbell et al. |
| 6,695,846 B2 | 2/2004 | Richelsoph et al. |
| 7,172,593 B2 | 2/2007 | Trieu et al. |
| 7,175,623 B2 * | 2/2007 | Thramann et al. ............ 606/294 |
| 7,229,443 B2 | 6/2007 | Eberlein et al. |
| 2001/0001119 A1 | 5/2001 | Lombardo |
| 2001/0041894 A1 | 11/2001 | Campbell et al. |
| 2002/0015189 A1 | 2/2002 | Miyajima |
| 2002/0120273 A1 | 8/2002 | Needham et al. |
| 2003/0040749 A1 | 2/2003 | Grabowski et al. |
| 2003/0060828 A1 | 3/2003 | Michelson |
| 2003/0078583 A1 | 4/2003 | Biedermann et al. |

* cited by examiner

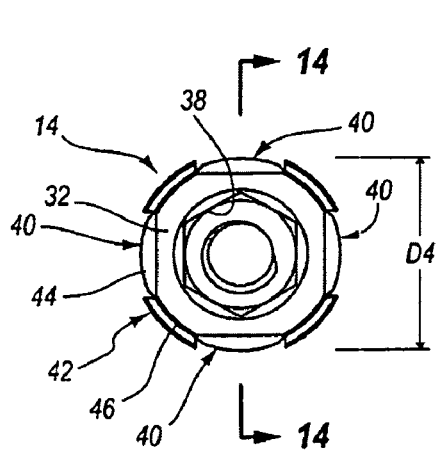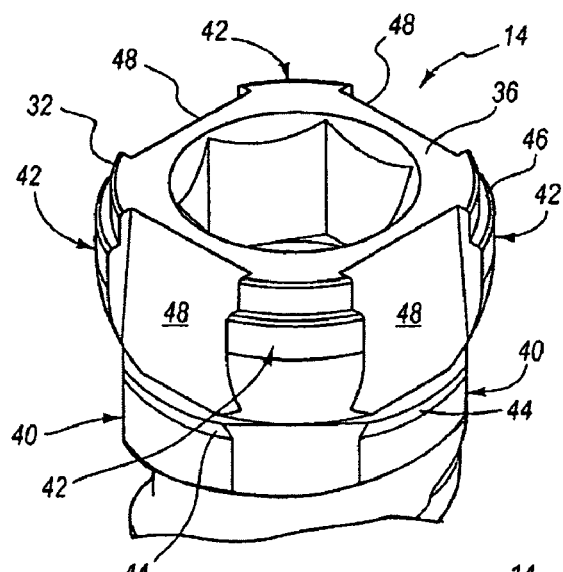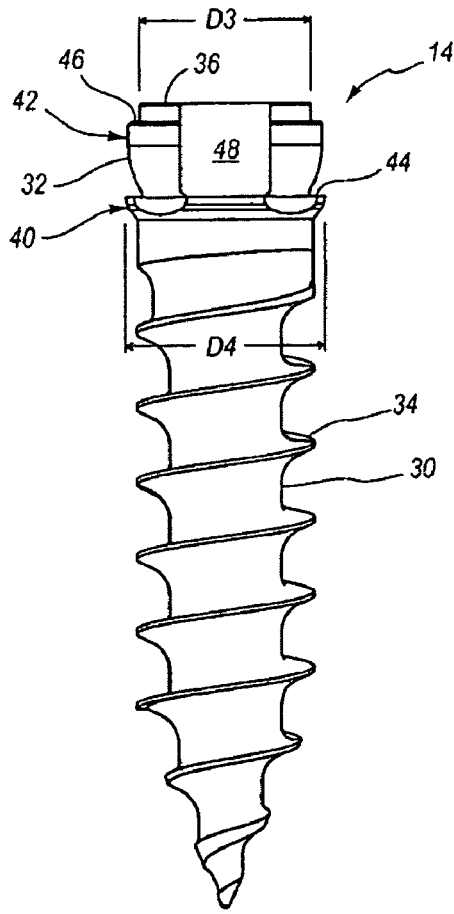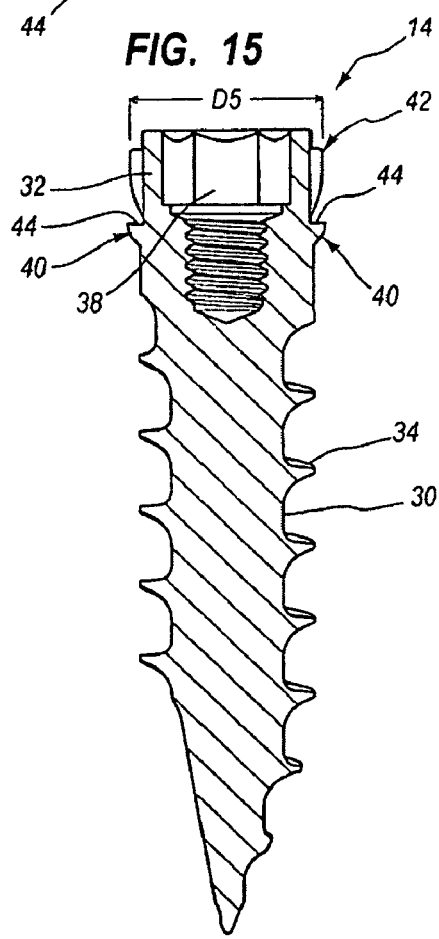
FIG. 13
FIG. 15
FIG. 12
FIG. 14

BONE PLATE ASSEMBLIES WITH BACKOUT PROTECTION AND VISUAL INDICATOR

FIELD OF THE INVENTION

The present disclosure generally relates to spinal implants and associated methods, and more particularly relates to bone plate assemblies having backout protection.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age, spinal discs begin to break down, or degenerate resulting in the loss of fluid in the discs and consequently resulting in them becoming less flexible. Likewise, the disks become thinner allowing the vertebrae to move closer together. Degeneration may also result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions are collectively referred to herein as spine disease.

Conventionally, surgeons treat spine disease by attempting to restore the normal spacing between adjacent vertebrae. This may be sufficient to relieve pressure from affected nerve tissue. However, it is often necessary to also surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

A plurality of bone screws may be used to secure a plate to the vertebrae. The bone screws, absent a screw retention mechanism, may back out or reverse thread. Screw retention mechanisms have been developed to inhibit the bone screws from backing out. Some of the devices include caps or plates that extend over the screw holes in the plate to inhibit upward movement of bone screws relative to the plate. Other devices include a frictional engagement between a bushing and the bone screws.

Although some devices exist for inhibiting backing out of bone screws, further advances in this area are possible.

SUMMARY

One aspect of the present disclosure relates to a bone plate assembly that includes a plate, at least one bushing, and at least one bone screw. The bushing is positioned within a through hole of the plate. The bushing and screw are configured to engage each other to inhibit the screw from backing out. The screw may include at least one visual indicator surface that is visible to the operator during insertion of the screw through the bushing and plate. The bushing is configured to cover at least a portion of the visual indicator surface to show the operator when the bushing and screw are properly engaged to inhibit backout of the screw.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings, which are incorporated in, and constitute a part of this specification, illustrate embodiments of the present invention, and together with the description, serve to explain the principles thereof. Like items in the drawings are referred to using the same numerical reference.

FIG. 12 is a side view of the screw of the bone plate assembly of FIG. 1;

FIG. 13 is a top view of the screw of the bone plate assembly of FIG. 1;

FIG. 14 is a cross-sectional view of the screw of the bone plate assembly of FIG. 1;

FIG. 15 is a close-up view of a head portion of the screw of FIG. 13;

DETAILED DESCRIPTION

The present disclosure is directed to a bone plate assembly that includes a bone plate, a bone screw, and a bushing member that provides backout protection for the screw relative to the plate. The example bushings disclosed herein not only provide backout protection for the screw, but may also provide a visual indicator to confirm when the screw has reached a locked position relative to the plate and bushing.

Figure 1:
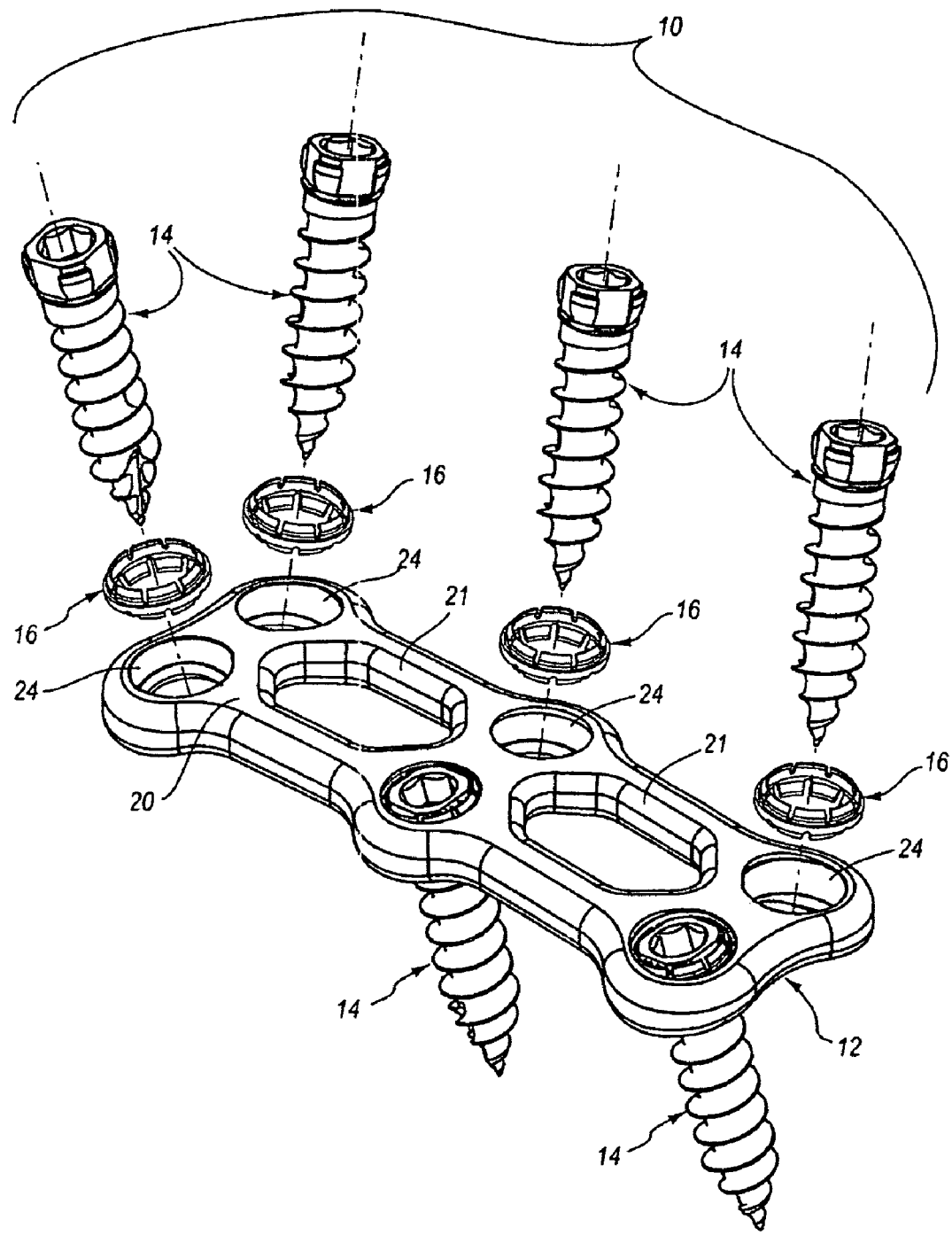
FIG. 1 is a partially exploded perspective view of a bone plate assembly according to the present disclosure.

An example bone plate assembly 10 is now described with reference to FIGS. 1-11. FIG. 1 illustrates a partially exploded view of the bone plate assembly 10 having a bone plate 12, a plurality of bushings 16, and a plurality of screws 14. Typically, the bushings 16 are mounted within through holes 24 of the plate 12, followed by insertion of the screws 14 into the bushings 16.

The bone plate 12 is shown having a construction that can span two intervertebral spaces (also known as a two level bone plate). However, bone plate 12 could be constructed to span more or fewer intervertebral spaces. Because plate 12 spans two intervertebral spaces, plate 12 is shown with two viewing windows 21 and through holes 24 corresponding to three vertebrae. More or fewer viewing windows 21 and through holes 24 may be provided in a single bone plate. For example, for a construction that spans only one intervertebral space, only one viewing window 21 and through holes 24 corresponding to 2 vertebrae may be used. Moreover, for a construction that spans three intervertebral spaces, three viewing windows 21 may be provided along with additional through holes 24. Furthermore, the window 21 may be split into a plurality of smaller windows as a matter of design choice.

Figure 4:
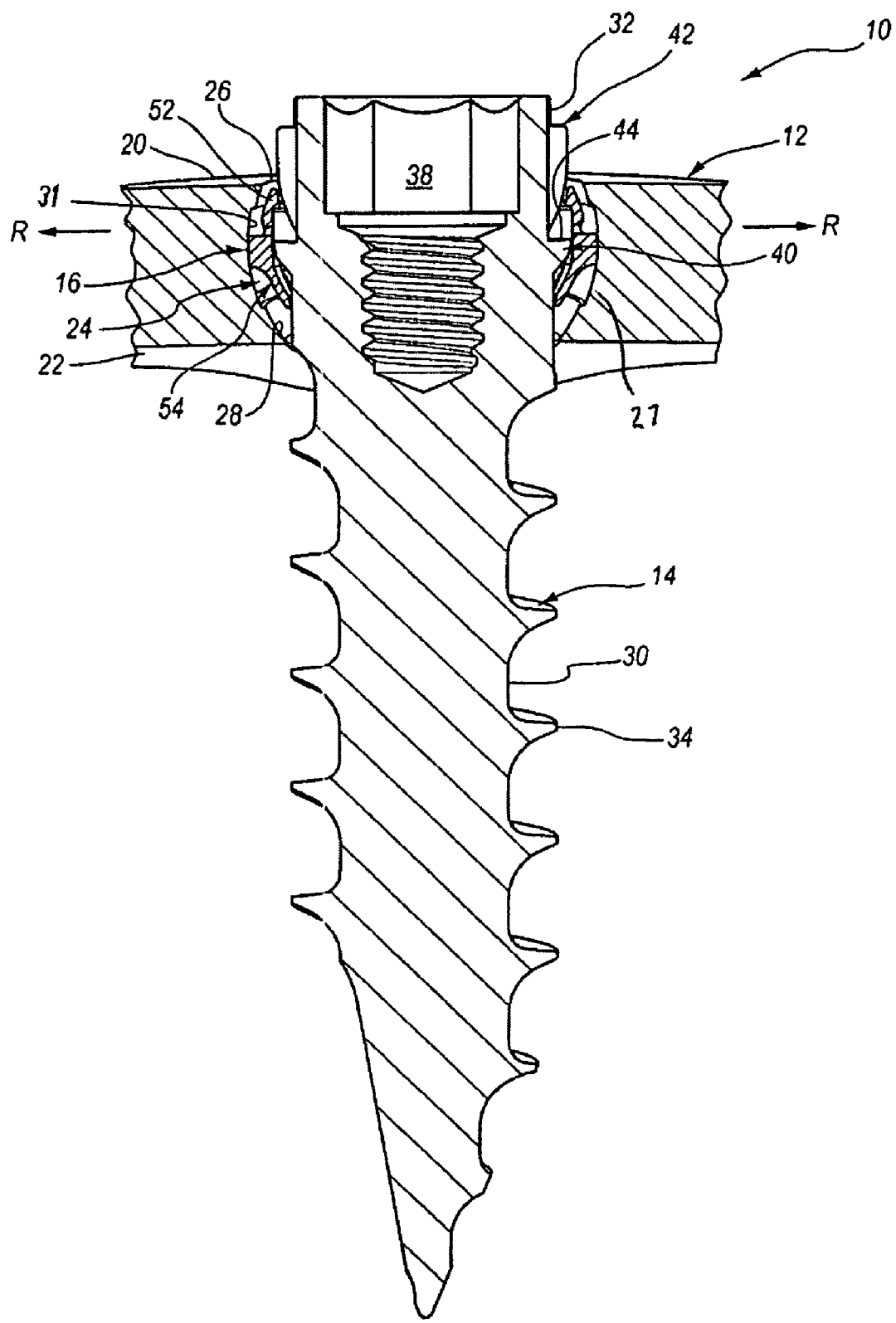
FIG. 4 is a cross-sectional view of the bone plate assembly of FIG. 1 with the screw in a first position.
Figure 5:
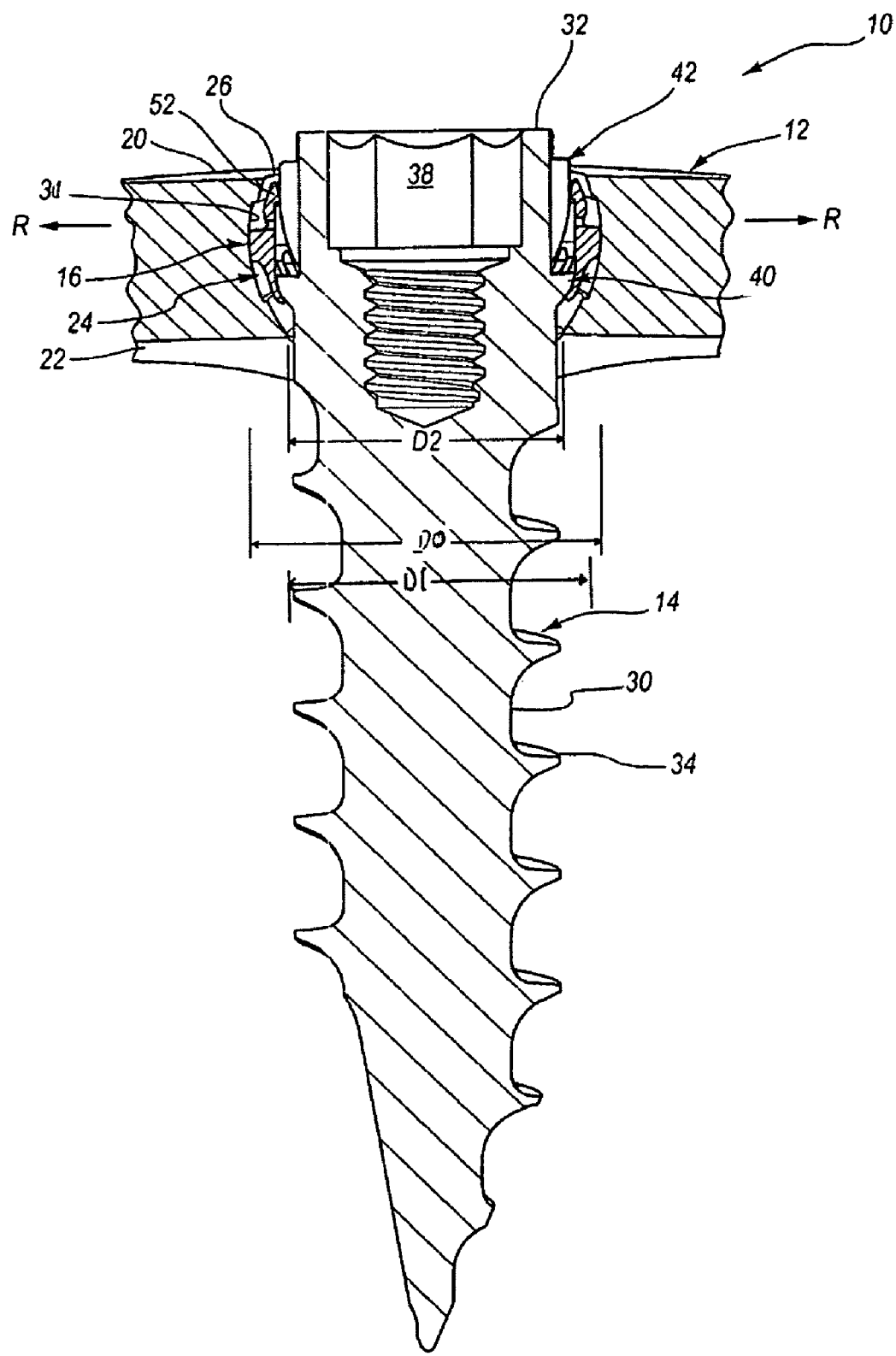
FIG. 5 is a cross-sectional view of the bone plate assembly of FIG. 1 with the screw in a second position.

A bone plate 12 includes a top surface 20 and a bottom or bone facing surface 22. The through holes 24 extend from the top surface 20 to the bottom surface 22. The through holes 24 include an entrance portion 26 and an exit portion 28. The through hole 24 has a contoured surface 31 about entrance portion 26. The contoured surface 31 about entrance portion 26 includes a generally spherical or contoured surface 31 with a first curvature radius having a maximum diameter or dimension D1. The surface 31 can also be described as a concave shaped surface 31. The entrance portion 26 is typically sized to receive and retain the bushing 16. The bushing 16 may need to be compressed or stressed to fit through entrance portion 26. As shown in FIGS. 4 and 5, through hole 24 may have a channel 27 formed in a portion of the through hole 24 between the entrance portion 26 and the exit portion 28. The channel 27 also may include a generally spherical or contoured surface 31 with a second curvature radius having a maximum diameter or dimension D0 generally greater than D1. As seen in cross section, this provides a step out like feature. Channel 27 is generally sized to receive the bushing 16 in an unstressed state. The exit portion 28 defines an exit diameter or dimension D2 adjacent to the bottom surface 20. Typically, the exit diameter D2 is sized smaller than a minimum width dimension of the head of the screw 14 such that only a shank portion of the screw 14 can pass through the through hole 24 and the head portion of the screw 14 is retained within the through hole 24. The exit portion may be described as a generally spherical or contoured surface having a third curvature radius. As seen in the cross section, the transition from channel 27 to exit portion 28 is a step in like feature.

Figure 2:
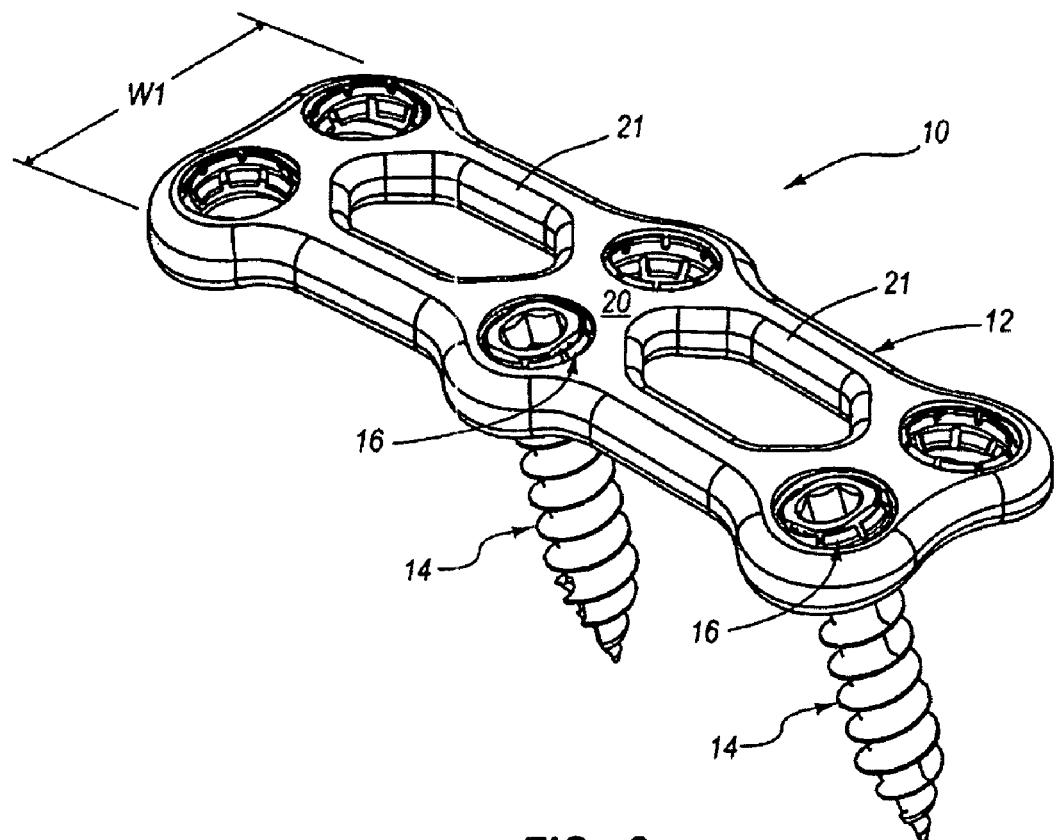
FIG. 2 is a top view of the bone plate assembly of FIG. 1 including two screws and two bushing members.
Figure 3:
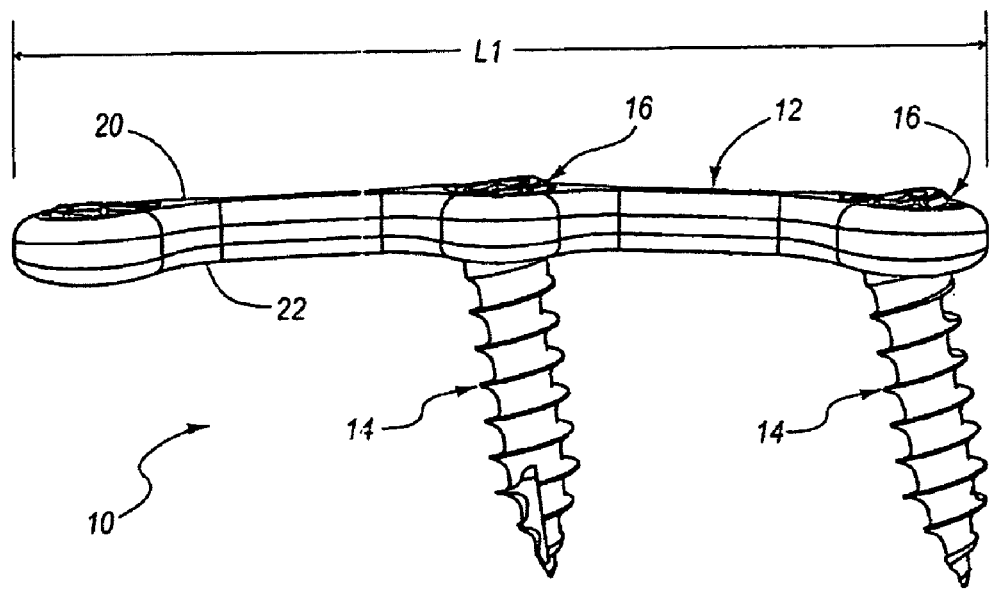
FIG. 3 is a side view of the bone plate assembly of FIG. 2.

Typically, the plate 12 has a length L1 and a width W1 as shown in FIGS. 2 and 3. Many other length and width configurations for the plate 12 are possible, such as plates shown in FIGS. 16A-D. While the various plates shown in FIGS. 16A-D have a relatively constant width W, the length varies for each plate. In other arrangements, not specifically shown, the length L can remain constant and the width W can vary. In yet other arrangements, both the width W and length L can vary among different bone plates.

The through holes 24 shown in FIGS. 1-3 have the same shape and size. In other arrangements, at least some of the through holes 24 have different sizes and shapes for a given plate 12 to accommodate different sized or shaped screws 14 or bushings 16.

Referring now to FIGS. 12-15, the screw 14 includes a shank 30, a head 32, a plurality of threads 34, a top surface 36, an instrument recess 38, a locking protrusion 40 located on an intermediate portion between the shank 30 and head 32, and a visual indicator protrusion 42. The head 32 has a plurality of spaced apart visual indicator protrusions 42. The visual indicator protrusions 42 have a maximum diameter or dimension D4 as shown in FIG. 14, and the top surface of the head has a smaller maximum diameter or dimension D3 as shown in FIG. 12. The intermediate portion about locking protrusion 40 has a maximum diameter or dimension D4 greater than D3 and D4. The plurality of threads 34 are positioned on the shank 30. The instrument recess 38 is defined in the top surface 36 and is sized to receive a portion of an installation instrument that can apply a twisting or torque force to the screw 14.

The locking protrusion 40 on the intermediate portion between the head 32 and the shank 30 may include a plurality of locking protrusion members 40 as shown in at least FIGS. 13-15. Each of the locking protrusions 40 includes a locking surface 44. The locking surface 44 is arranged generally perpendicular to a longitudinal dimension of the screw 14. The orientation of the locking surface 44 may also be defined as facing a direction opposite the direction of insertion of the screw 14 into the plate 12. Other shapes and sizes for the locking surface 44 are possible. The locking protrusions 40 may define a maximum width dimension D4 measured from an outer surface of one locking protrusion (i.e., furthest radial outward surface) to an outer surface of a locking protrusion positioned on an opposite side of the screw 14.

A visual indicator protrusion 42 may include a plurality of spaced apart visual indicator protrusions 42 arranged around a periphery of the head 32 as shown in at least FIGS. 13 and 15. Each of the visual indicator protrusions 42 defines a visible surface or shelf 46. The visual surface 46 is shown arranged generally perpendicular to a longitudinal axis of the screw 14. Visual surface 46 also may be defined as facing a direction opposite the direction of insertion of the screw 14 into the plate 12. Typically, the entire visual surface 46 is visible from the end view shown in FIG. 13. The visual indicator protrusions 42 define a maximum width dimension D5 extending from an outer surface of one visual indicator protrusion 42 (i.e., furthest radial outward surface) to an outer surface of a visual indicator protrusion 42 in an opposite side of the head 32 (see FIG. 14). Covering or exposing portions of the visual surfaces 46 while implanting the bone plate assembly 10 in a patient may provide a visual indication to the operator concerning certain orientations of the screw 14 relative to the plate 12 and bushing 16.

The screw 14 also may include at least one release instrument recess 48 around a periphery of the head 32. The release instrument recess 48 may provide space for a portion of an instrument or device to be inserted between the head 32 and the bushing 16 after the screw 14 has been locked into the bushing 16 (i.e., in the locked position shown in FIGS. 2, 3 and 6). The inserted release instrument or device positioned within the release instrument recess 48 may release or otherwise disengage the screw 14 from the bushing 16 to permit backing out of the screw 14.

Referring now to FIGS. 8-11, the bushing 16 includes a base portion 50, a plurality of top tab members 52, and a plurality of bottom tab members 54. The base portion 50 defines a ring structure from which the top and bottom tab members 52, 54 extend in opposite directions. The base portion 50 defines an outer contact surface 56 that defines a maximum outer diameter or dimension D6 (see FIG. 10). Typically, the diameter D6 is substantially equal to the maximum internal diameter D1 of the entrance portion 26 of the through hole 24. In some arrangements, the outer contact surface 56 has a generally contoured shape to facilitate easier insertion of the bushing 16 into the entrance portion 26 through the opening of the through holes 24 along the top surface 20. The bushing 16 may be compressible such that the bushing 16 may be compressed to fit through the opening into entrance portion 26. To assist with compression, the bushing 16 may include a gap (not shown). Once a compressive force that is used to compress the bushing 16 is removed (i.e., typically after the bushing 16 is positioned within the entrance portion 26), the bushing 16 expands such that the outer contact surface 56 cooperatively engages the spherical surface 30 within the entrance portion 26.

The bushing 16 includes a generally shape that matches the contoured surface 30 of the channel 27 between the entrance portion 26 and exit portion 28. In general, the bushing 16 has a shape that cooperatively engages the channel 27 and may allow polyaxial orientation of bushing 16 relative to plate 12. The spherical shape of the channel 27 may permit some movement of the base portion 50 within the channel 27. In some arrangements, the bushing 16 may be able to tilt or rock back and forth within the channel 27 depending on an orientation of the screw 14 relative to the plate 12. FIG. 1 illustrates how the screws 14 may be inserted into the plate 12 at different relative angles. The entrance portion 26 and exit portion 28 of the through holes 24 may be configured to permit various orientations of the screws 14 while still permitting operation of the bushing 16 to lock the screws 14 within the through holes 24 of the plate 12.

The top tab members 52 are spaced apart around a periphery of the base portion 50 and extend in a vertically upward direction (i.e., a direction toward the top surface 20 of the plate 12). The top tab members 52 define a top edge or surface 58 of the bushing 16. A plurality of dividing slots 60 may be used to define or space apart adjacent top tab members 52. Each of the top tab members 52 may include a screw contact surface 62 that is arranged facing generally radially inward towards the screw as the screw passes through the bushing 16. The top tab members 52 may also include an undercut surface 64 as shown in the detailed view of FIG. 11.

Figure 10:
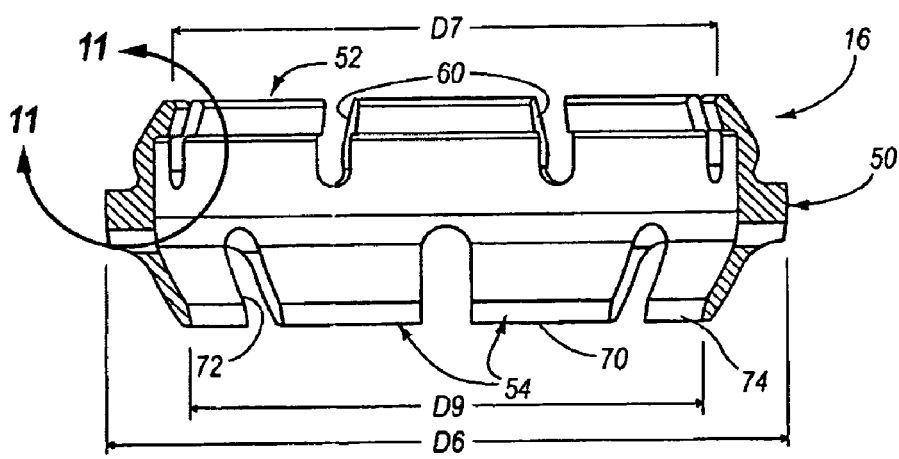
FIG. 10 is a cross-sectional view of the bushing of the bone plate assembly of FIG. 1.
Figure 11:
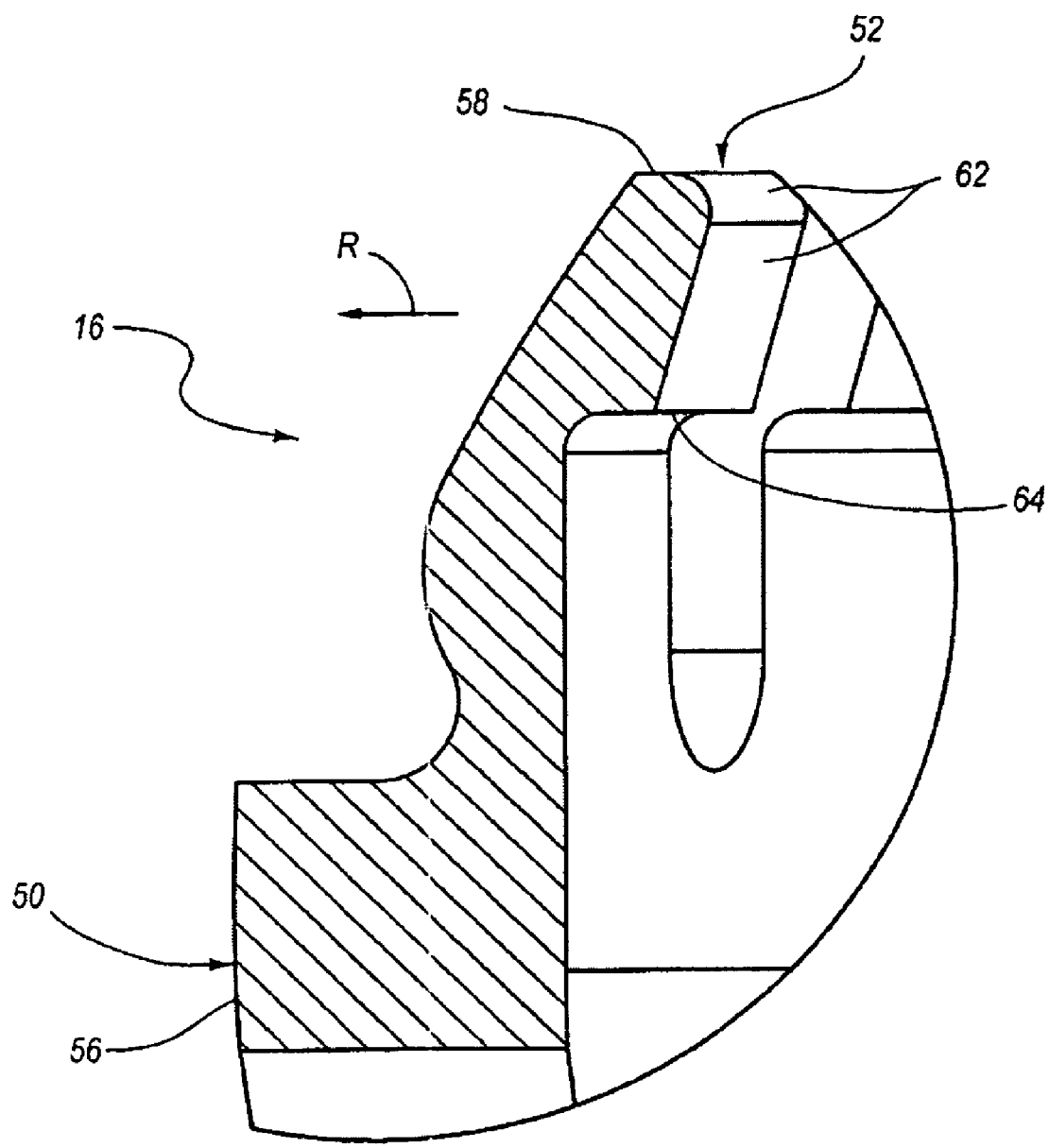
FIG. 11 is a close up view of a portion of the bushing shown in FIG. 9.
Figure 16A:
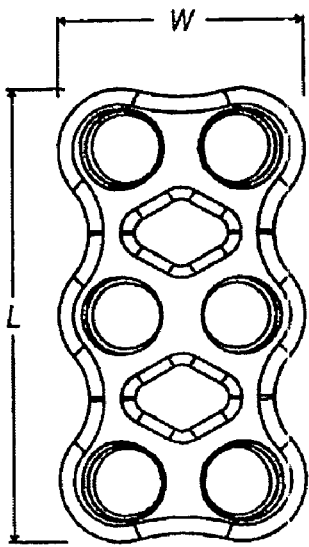
FIGS. 16A-D are top views of several alternative plate embodiments for use with the bone plate assembly of FIG. 1.
Figure 16B:
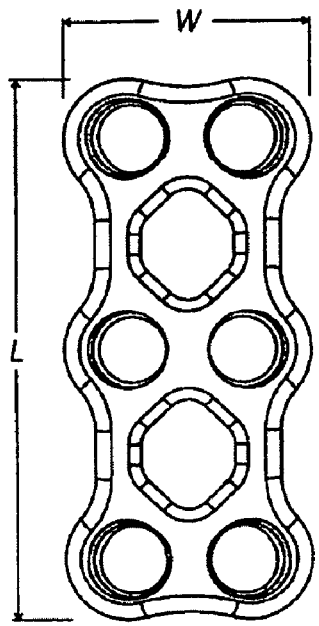
Figure 16C:
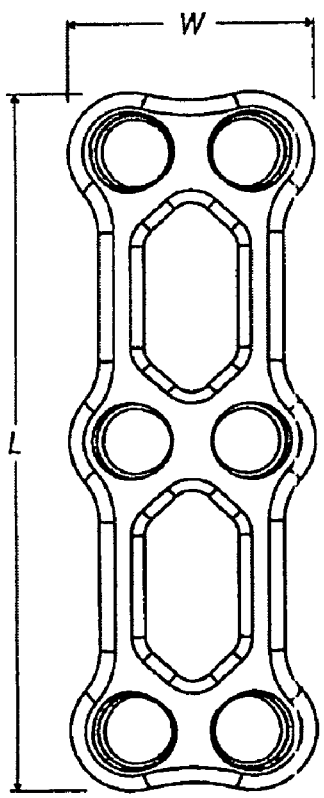
Figure 16D:
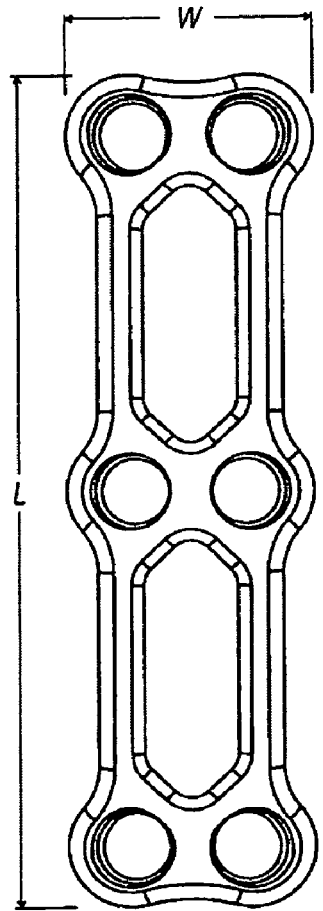

The top tab members 52 define an internal diameter or dimension D7 between the screw contact surface 62 of opposing top tab members 52 (see FIG. 10). The dimension D7 defines a minimum opening size into the bushing 56 when the top tab members 52 are in an unflexed or rest state. As the screw 14 passes through the bushing 16 as shown in FIGS. 4 and 5, the screw contact surfaces 62 engage a radially outward facing surface of the visual indicator protrusions 42 thereby flexing the top tab members 52 radially outward in the direction R. Typically, the dimension D7 is equal to or greater than the maximum dimension D3 of the head 32 of the screw 14. The top tab members 52 typically maintain the rest or unflexed state until being engaged by the visual indicator protrusions 42. The indicia of visual indicator protrusions 42 may be, for example, a surface color, a surface texture, or the like.

Figure 6:
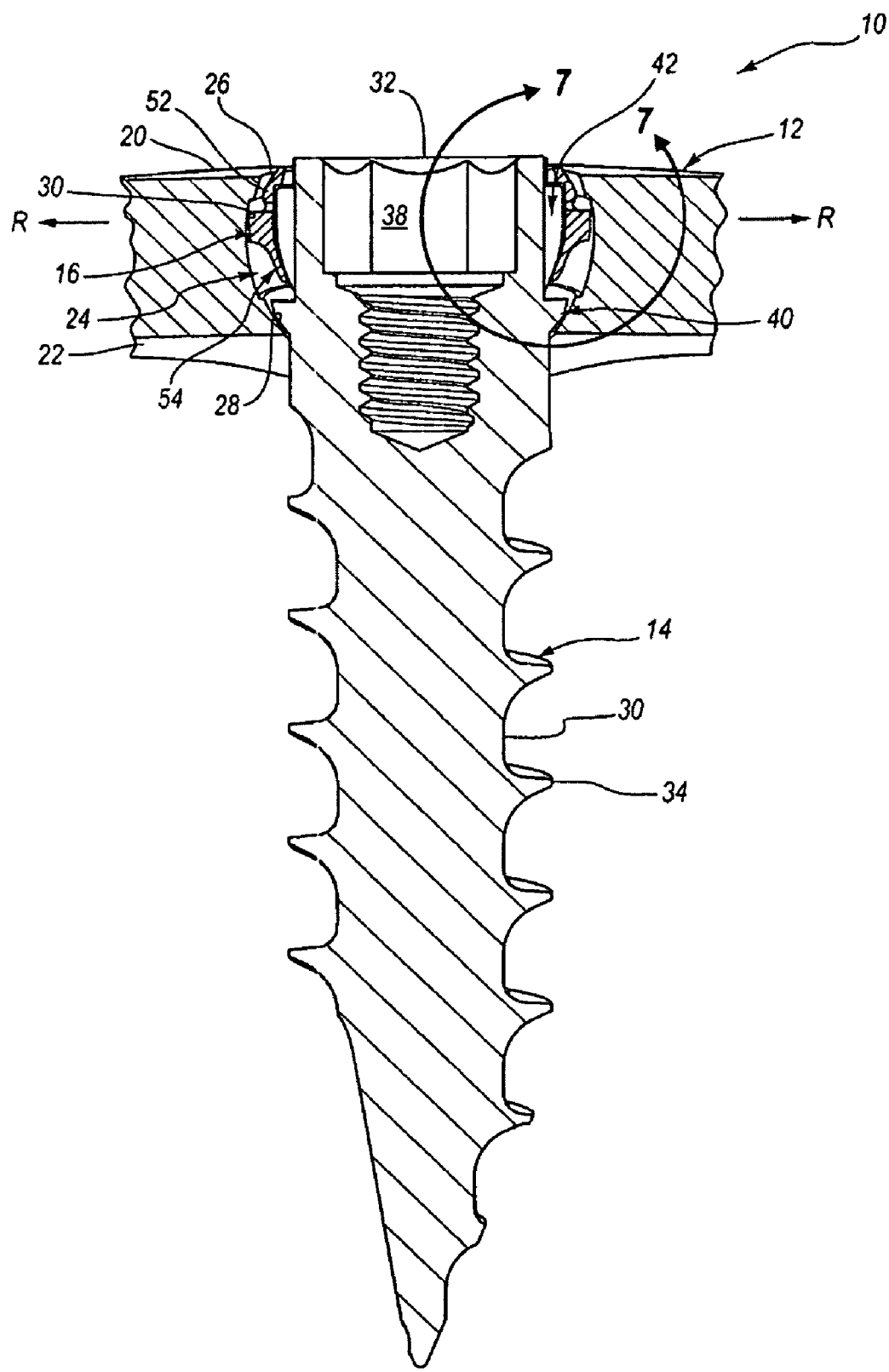
FIG. 6 is a cross-sectional view of the bone plate assembly of FIG. 1 with the screw in a third position.
Figure 7:
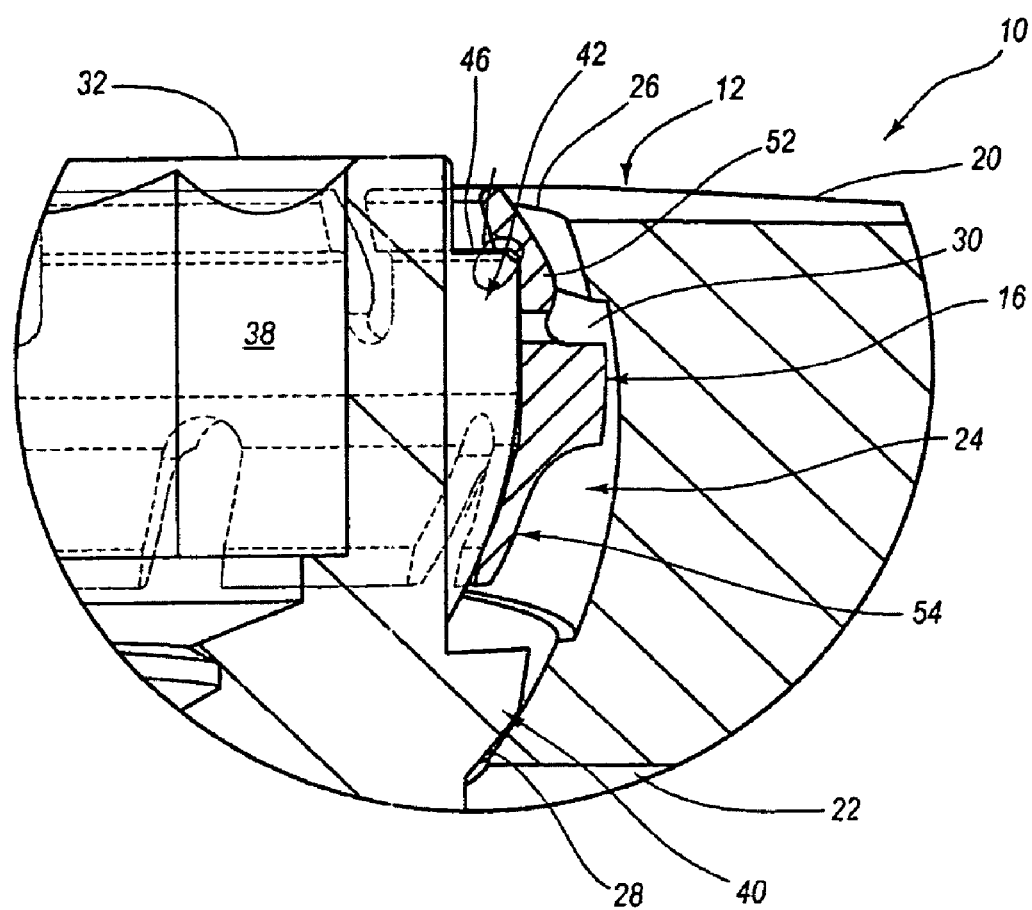
FIG. 7 is a close up view of a portion of the bone plate assembly of FIG. 6.
Figure 9:
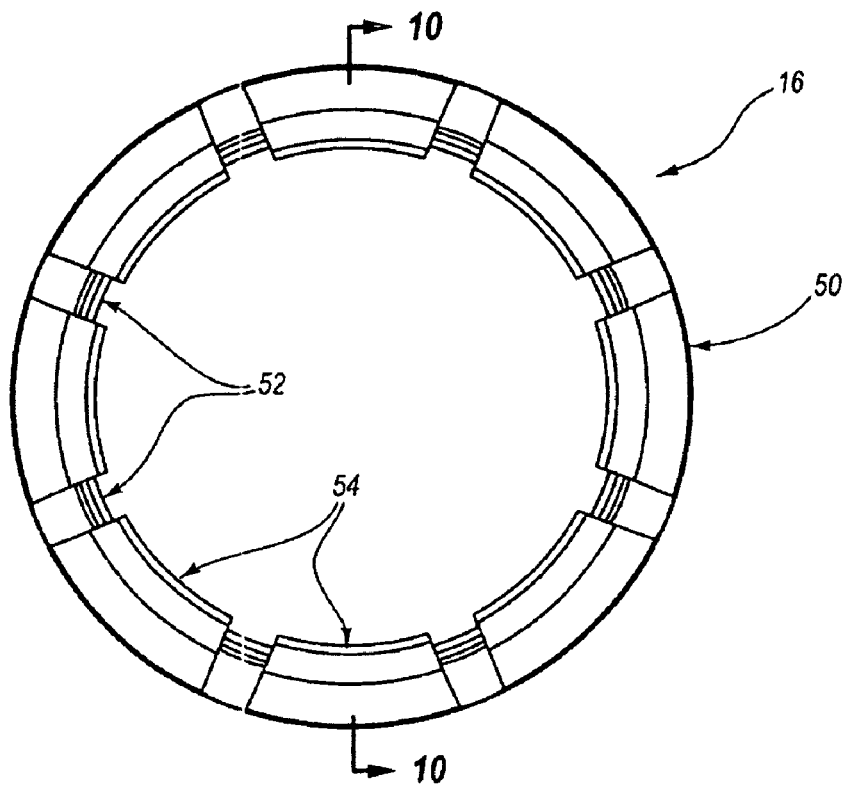
FIG. 9 is a top view of the bushing of the bone plate assembly of FIG. 1.
Figure 8:
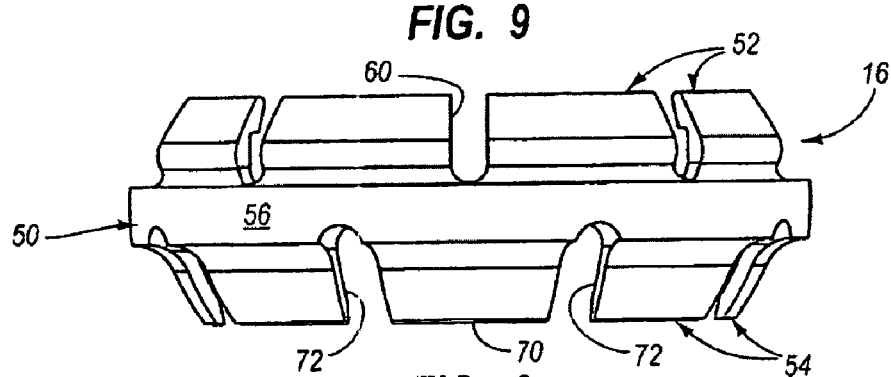
FIG. 8 is a side view of the bushing of the bone plate assembly of FIG. 1.

Once the visual indicator protrusions 42 have moved axially through the bushing 16 past the undercut surface 64 such that a gap will exist between the visual indicator protrusion 42 and undercut surface 64, the top tab members 52 move from the flexed state shown in FIG. 5 to the unflexed state shown in FIG. 6, thereby inhibiting the viewing of at least a portion of the visual surface or shelf 46. While it is preferable to provide the gap, undercut surface 64 and visual indicator protrusion 42 may abut. As the screw 14 passes through the bushing 16, the entire visual surface 46 is usually visible to the operator until at least a portion of the visual indicator protrusion 42 moves past the undercut surface 64. At this point, at least some portions of the top tab members 52 are inhibiting the viewing of at least some portion or portions of the visual surface 46 as viewed from an end view of the screw 14. This inhibiting of the viewing of portions of the visual surface 46 by the top tab members 52 provides a visual indication to the operator that the screw has obtained a certain axial position relative to the bushing 16.

The axial position of the visual indicator protrusion 42 when positioned axially past the undercut surface 64 is subsequent to or coincides with the locking engagement of the bottom tab members 54 with the locking protrusion 40 of the screw 14. The bottom tab members 54 are spaced apart around a periphery of the base portion 50 and extend in a downward direction (i.e., in a direction facing toward the bottom surface 22 of the plate 12). The bottom tab members 54 define a bottom edge 70 of the bushing 16. The bottom edge 70 also defines a locking contact surface for engagement with the locking surface 44 of the locking protrusions 40. A plurality of dividing slots 72 extend from the bottom edge 70 toward the base portion 50 to space apart or divide adjacent tab members 54. The locking protrusion preferably resides between the head and the threaded portion of the shank.

The bottom tab members 54 also define a screw contact surface 74 that faces generally radially inward. The screw contact surface 74 is arranged to contact a radially outward facing surface of the locking protrusions 40 as the screw 14 moves axially through the bushing 16. The bottom tab members 54 define a maximum inner diameter or dimension D9 measured between the screw contact surface 74 of opposing tab members as shown in at least FIG. 10. An example back-out protection bushing, having a plurality of bottom tab members, is described in U.S. Pat. No. 7,175,623, which is incorporated herein by reference in its entirety.

Referring now to FIGS. 4-7, a method of inserting and locking a screw 14 relative to the plate 12 is described. The bushing 16 is first inserted into the through hole 24 of the plate 12 as shown in FIG. 4. The bushing 16 is typically inserted during manufacturing or at least pre-surgery. The screw 14 is inserted into the bushing 16 until the locking protrusion 40 begins to engage the screw contact surface 74 of bottom tab members 54, and the visual indicator protrusion 42 begins to engage the screw contact surface 62 of the top tab members 52 (see FIG. 5). Further insertion of the screw 14 through the bushing 16 causes flexing of the top tab members 52 and bottom tab members 54 in a radially outward direction R by engagement with radially outward facing surfaces of the visual indicator protrusions 42 and locking protrusion 40, respectively. During insertion of the screw 14, the visual surface 46 is visible to the operator from an end view (i.e., the view of FIG. 13).

The screw 14 attains a locked position when the locking protrusions 40 have moved axially past the bottom edge 70 of the bottom tab members 54 so that the bottom edge 70 contacts the locking surface 44 of locking protrusions 40. Concurrently or subsequently, the visual indicator protrusions 42 move past the undercut surface 64 of the top tab members 52 so that the undercut surface 64 faces and resides above the visual surface 46 (see FIGS. 6-7). In at least some arrangements, no portion of the top tab members 52 engages the screw 14 when the screw is in the locked position. When in the locked position, at least some portions of the visual surface 46 are obstructed from the operator's view. In some arrangements, the bushing 16 when locked is in an unstressed condition and no part of the screw flexes or stresses the bushing 16.

The screw 14 is prevented from backing out or unscrewing relative to the plate 12 by the placement of the bottom edge 70 of the bottom tab members 54 above the locking surface 44 of the locking protrusion 40 on the screw 14. In other words, if the screw backs out, the locking surface 44 will not be able to move past bottom edge 70 in the normal course inhibiting the amount of backing out, although some reverse threading may be possible as bottom edge 70 may be positioned a distance from locking surface 44.

In some arrangements, reverse screwing (i.e., backing out) of the screw 14 may be accomplished if the bottom tab members 54 are flexed outward in the direction R to at least a dimension D4. Such flexing of the bottom tab members 54 may be accomplished by inserting a release tool into at least one of the released instrument recesses 48 defined on the head 32 of the screw 14.

While the above figures show a plate extending over one level, one of ordinary skill in the art will recognize on reading the disclosure that the present invention would be useful for multiple level fusions. Moreover, although the stabilization device is depicted extending from a single end of the plate, one of ordinary skill in the art on reading the disclosure would understand that the present invention could have stabilization devices extending from multiple connection points, i.e., the superior and inferior direction.

While the invention has been particularly shown and described with reference to embodiments thereof, it will be understood by those skilled in the art that various other changes in the form and details may be made without departing from the spirit and scope of the invention.

We claim:

1. A bone plate assembly, comprising:
    a bone plate having a plurality of through holes;
    a bushing retained in one of the plurality of through holes, the bushing including:
        at least one flexible bottom tab member arranged along a bottom portion of the bushing;
        a plurality of flexible top tab members arranged along a top portion of the bushing;
    a screw, comprising:
        a locking protrusion including a locking surface; and
        a visual indicator protrusion;
    wherein the locking protrusion engages the bottom tab member to flex the bottom tab member radially outward and the visual indicator protrusion engages each of the plurality of flexible top tab members to flex each of the plurality of flexible top tab members radially outward as the screw passes through the bushing, the locking surface engaging the bottom tab member after the locking protrusion moves axially past the bottom tab member into a locked position to inhibit the screw from reverse movement out of the through hole, and at least one of the plurality of flexible top tab members covering at least a portion of the visual indicator protrusion when the bottom tab member is in the locked position.

2. The bone plate assembly of claim 1, wherein the bottom tab member returns to an unflexed position when the locking protrusion moves axially past the bottom tab member.

3. The bone plate assembly of claim 1, wherein the bottom tab member defines a bottom edge of the bushing and the plurality of flexible top tab members defines a top edge of the bushing.

4. The bone plate assembly of claim 1, wherein the screw includes a head portion, a shaft portion, and an intermediate portion connecting the head portion and the shaft portion, the locking protrusion extending radially outward from the intermediate portion and the visual indicator protrusion extending radially outward from the head portion.

5. The bone plate assembly of claim 1, wherein a surface of the visual indicator protrusion is visible during insertion of the screw until the locking protrusion attains the locked position.

6. The bone plate assembly of claim 1, wherein the plurality of flexible top members and at least one flexible bottom tab members are axially spaced apart from each other.

7. The bone plate assembly of claim 1, wherein the locking protrusion includes a locking surface arranged generally perpendicular to an axis of the through hole and a portion of the bottom tab member contacts the locking surface when the bottom tab member is in the unflexed position.

8. The bone plate assembly of claim 1, wherein the visual indicator protrusion does not engage an undercut of the plurality of flexible top tab members when in the unflexed position.

9. An implantable device for affixing to a vertebrae, comprising:
    a plate member including:
        an anterior surface and a posterior surface;
        a plurality of holes extending from the anterior surface to the posterior surface, each hole including an entrance portion, a channel, and an exit portion, the exit portion including having an exit diameter;
    a screw including:
        a shank portion sized to extend through the exit portion of the hole; and
        a head portion including at least one visual indicator protrusion; and
        an intermediate portion between the head portion and the shank portion including at least one locking protrusion that is separate from the at least one visual indicator protrusion, the intermediate portion being sized greater than the exit diameter; and
    a bushing member positioned in the hole, the bushing member includes at least one top tab member that includes an undercut surface that remains out of contact with the screw when the bottom tab member is in the locked position and is arranged adjacent to the anterior surface and at least one bottom tab member arranged adjacent to the posterior surface, the top and bottom tab members flexing radially outward as the head portion passes into the bushing, a portion of the top tab member obstructing the visual indicator protrusion when the bottom tab member engages the locking protrusion in a locked position.

10. The implantable device of claim 9, wherein the locking protrusion includes a locking surface that is arranged generally perpendicular to a direction of insertion of the screw into the bushing, the locking surface of the locking protrusion engages the bottom tab member when the bottom tab member is in the locked position.

11. The implantable device of claim 9, wherein the bottom tab member engages a locking surface of the locking protrusion after the locking protrusion moves axially past the bottom tab member and the bottom tab member returns to an unflexed position.

12. The implantable device of claim 9, wherein the top tab member remains out of contact with the screw after the top tab member returns to an unflexed position and the bottom tab member is in the locked position.

13. The implantable device of claim 9, wherein the entrance portion includes a partial spherical shape, and the bushing member has a contoured outer surface that contacts the entrance portion of the hole.

14. A bone plate assembly, comprising:
    a bone plate having a plurality of through holes;

a bushing retained in one of the plurality of through holes, the bushing including:
- at least one flexible bottom tab member arranged along a bottom portion of the bushing;
- at least one flexible top tab member arranged along a top portion of the bushing;

a screw, comprising:
- a locking protrusion including a locking surface; and
- a visual indicator protrusion;
- wherein the locking protrusion engages the bottom tab member to flex the bottom tab member radially outward and the visual indicator protrusion engages the top tab member to flex the top tab member radially outward as the screw passes through the bushing, the locking surface engaging the bottom tab member after the locking protrusion moves axially past the bottom tab member into a locked position to inhibit the screw from reverse movement out of the through hole, and the top tab member covering at least a portion of the visual indicator protrusion when the bottom tab member is in the locked position and wherein the top tab member includes an undercut surface arranged generally perpendicular to a direction of insertion of the screw, the top tab member returning to an unflexed position when the visual indicator protrusion moves axially past the undercut surface.

15. The bone plate assembly of claim 14, wherein the undercut surface of the top tab member is spaced axially from a top edge of the bushing.

16. A method of assembling a bone plate assembly, the bone plate assembly including a plate having a plurality of through holes, a bushing arranged in one of the through holes and having top and bottom flexible tab members where the top flexible tab member includes an undercut surface, and a screw having a locking protrusion and a visual indicator protrusion, the method including:
- contacting the visual indicator protrusion and locking protrusion with the top and bottom tab members, respectively, to flex the top and bottom tabs radially outward;
- axially advancing the screw through the bushing until the locking protrusion moves axially past the bottom tab member to position the screw in a locked state, and until the top tab member overlaps a portion of the visual indicator protrusion by returning to an unflexed position.

17. The method of claim 16, wherein the bottom tab member returns to an unflexed position after the locking protrusion moves axially past the bottom tab member.

18. The method of claim 16, wherein the top and bottom tab members are axially spaced apart on the bushing, the top tab member defining a top edge of the bushing and the bottom tab member defining a bottom edge of the hushing, and the bottom edge of the bushing engages a locking surface of the locking protrusion after the locking protrusion moves axially past the bottom tab member.

19. The method of claim 16, wherein the top tab member overlaps a surface of the visual indicator protrusion that is visible by an operator from an end view of the screw until the screw reaches the locked state.

\* \* \* \* \*